US008571880B2

(12) United States Patent
Goldberg

(10) Patent No.: US 8,571,880 B2
(45) Date of Patent: Oct. 29, 2013

(54) PERSONAL HEALTH MANAGEMENT DEVICE, METHOD AND SYSTEM

(75) Inventor: Jason Goldberg, Ontario (CA)

(73) Assignee: Ideal Life, Inc., Toronto (CA)

( * ) Notice: Subject to any disclaimer, the term of this patent is extended or adjusted under 35 U.S.C. 154(b) by 1954 days.

(21) Appl. No.: 10/913,140

(22) Filed: Aug. 6, 2004

(65) Prior Publication Data

US 2005/0071197 A1  Mar. 31, 2005

Related U.S. Application Data

(60) Provisional application No. 60/493,904, filed on Aug. 7, 2003.

(51) Int. Cl.
*G06Q 10/00* (2012.01)
*A61B 5/00* (2006.01)
*G08C 19/16* (2006.01)

(52) U.S. Cl.
USPC ................ 705/2; 600/300; 340/870.01

(58) Field of Classification Search
USPC ................ 705/2; 600/300; 340/870
See application file for complete search history.

(56) References Cited

U.S. PATENT DOCUMENTS

| | | | |
|---|---|---|---|
| 3,804,524 A | 4/1974 | Jocoy et al. | |
| 4,394,773 A | 7/1983 | Ruell | |
| 4,408,323 A | 10/1983 | Montgomery | |
| 4,453,247 A | 6/1984 | Suzuki et al. | |
| 4,581,735 A | 4/1986 | Flamm et al. | |
| 4,731,726 A | 3/1988 | Allen, III | |
| 4,782,485 A | 11/1988 | Gollub | |
| 4,831,242 A * | 5/1989 | Englehardt et al. | 235/382 |
| 4,857,916 A | 8/1989 | Bellin | |
| 4,905,293 A | 2/1990 | Asai et al. | |
| 4,914,650 A | 4/1990 | Sriram | |
| 5,144,680 A | 9/1992 | Kobayashi et al. | |
| 5,213,555 A * | 5/1993 | Hood et al. | 482/57 |
| 5,307,263 A | 4/1994 | Brown | |

(Continued)

FOREIGN PATENT DOCUMENTS

| | | |
|---|---|---|
| WO | WO 01/65810 A1 | 9/2001 |
| WO | WO 01/97703 A2 | 12/2001 |

OTHER PUBLICATIONS

Hardesty, Larry, "Clothed in Health," Technology Review, Jul./Aug. 2001, p. 34.

(Continued)

*Primary Examiner* — Calvin L Hewitt, II
*Assistant Examiner* — Zeshan Qayyum
(74) *Attorney, Agent, or Firm* — Frank J. DeRosa; Frommer Lawrence & Haug LLP

(57) ABSTRACT

The present invention generally provides personal health management devices, and corresponding systems and methods. The personal health management device generally include an electronic controller and at least one memory device which cooperate to store at least temporarily weight management data for managing the weight of at least one user, such as a user's weight, a user's body fat percentage, exercise data, food consumption data, or a combination thereof, obtained from at least one component for obtaining such data, such as a keypad, a body fat percentage sensor for measuring a user's body fat percentage, a scale for measuring a user's weight, an exercise machine, a food scale, etc., and a communications unit for communicating the data obtained to a healthcare provider for monitoring progress with respect to a weight management program over a communications network.

5 Claims, 3 Drawing Sheets

(56) References Cited

U.S. PATENT DOCUMENTS

| | | |
|---|---|---|
| 5,390,238 A | 2/1995 | Kirk et al. |
| 5,412,463 A | 5/1995 | Sibbald et al. |
| 5,420,936 A | 5/1995 | Fitzpatrick et al. |
| 5,467,403 A | 11/1995 | Fishbine et al. |
| 5,546,471 A | 8/1996 | Merjanian |
| 5,576,952 A | 11/1996 | Stutman et al. |
| 5,603,179 A | 2/1997 | Adams |
| 5,617,423 A | 4/1997 | Li et al. |
| 5,687,732 A | 11/1997 | Inagaki et al. |
| 5,701,904 A | 12/1997 | Simmons et al. |
| 5,704,366 A | 1/1998 | Tacklind et al. |
| 5,713,350 A | 2/1998 | Yokota et al. |
| 5,732,133 A | 3/1998 | Mark |
| 5,772,586 A | 6/1998 | Heinonen et al. |
| 5,796,858 A | 8/1998 | Zhou et al. |
| 5,822,715 A | 10/1998 | Worthington et al. |
| 5,827,180 A | 10/1998 | Goodman |
| 5,828,943 A | 10/1998 | Brown |
| 5,832,448 A | 11/1998 | Brown |
| 5,838,306 A | 11/1998 | O'Connor et al. |
| 5,840,020 A | 11/1998 | Heinonen et al. |
| 5,852,670 A | 12/1998 | Setlak et al. |
| 5,862,803 A | 1/1999 | Besson et al. |
| 5,872,834 A | 2/1999 | Teitelbaum |
| 5,875,430 A * | 2/1999 | Koether ............ 705/15 |
| 5,879,163 A | 3/1999 | Brown et al. |
| 5,897,493 A | 4/1999 | Brown |
| 5,899,855 A | 5/1999 | Brown |
| 5,910,946 A | 6/1999 | Csapo |
| 5,920,642 A | 7/1999 | Merjanian |
| 5,926,261 A | 7/1999 | Hoshino |
| 5,933,136 A | 8/1999 | Brown |
| 5,940,801 A | 8/1999 | Brown |
| 5,950,632 A | 9/1999 | Reber et al. |
| 5,951,300 A | 9/1999 | Brown |
| 5,953,322 A | 9/1999 | Kimball |
| 5,956,501 A | 9/1999 | Brown |
| 5,957,854 A | 9/1999 | Besson et al. |
| 5,960,403 A | 9/1999 | Brown |
| 5,970,458 A | 10/1999 | Petkovset |
| 5,985,559 A | 11/1999 | Brown |
| 5,991,408 A | 11/1999 | Pearson et al. |
| 5,997,476 A | 12/1999 | Brown |
| 6,011,860 A | 1/2000 | Fujieda et al. |
| 6,016,476 A | 1/2000 | Maes et al. |
| 6,024,699 A | 2/2000 | Surwit et al. |
| 6,028,950 A | 2/2000 | Merjanian |
| 6,032,119 A | 2/2000 | Brown et al. |
| 6,047,203 A | 4/2000 | Sackner et al. |
| 6,050,940 A | 4/2000 | Braun et al. |
| 6,064,737 A | 5/2000 | Rhoads |
| 6,072,396 A | 6/2000 | Gaukel |
| 6,078,848 A | 6/2000 | Bernstein et al. |
| 6,078,908 A | 6/2000 | Schmitz |
| 6,088,585 A | 7/2000 | Schmitt et al. |
| 6,101,478 A | 8/2000 | Brown |
| 6,111,977 A | 8/2000 | Scott et al. |
| 6,121,247 A | 9/2000 | Huang et al. |
| 6,128,563 A | 10/2000 | Muraro |
| 6,135,951 A | 10/2000 | Richardson et al. |
| 6,141,436 A | 10/2000 | Srey et al. |
| 6,144,837 A | 11/2000 | Quy |
| 6,151,586 A | 11/2000 | Brown |
| 6,160,903 A | 12/2000 | Hamid et al. |
| 6,161,095 A | 12/2000 | Brown |
| 6,167,362 A | 12/2000 | Brown et al. |
| 6,168,563 B1 | 1/2001 | Brown |
| 6,175,752 B1 | 1/2001 | Say et al. |
| 6,175,922 B1 | 1/2001 | Wang |
| 6,177,950 B1 | 1/2001 | Robb |
| 6,191,410 B1 | 2/2001 | Johnson |
| 6,196,970 B1 | 3/2001 | Brown |
| 6,219,793 B1 | 4/2001 | Li et al. |
| 6,221,010 B1 | 4/2001 | Lucas |
| 6,240,393 B1 | 5/2001 | Brown |
| 6,246,992 B1 | 6/2001 | Brown |
| 6,248,065 B1 | 6/2001 | Brown |
| 6,249,672 B1 | 6/2001 | Castiel |
| 6,256,737 B1 | 7/2001 | Bianco et al. |
| 6,260,022 B1 | 7/2001 | Brown |
| 6,270,455 B1 | 8/2001 | Brown |
| 6,282,304 B1 | 8/2001 | Novikov et al. |
| 6,289,238 B1 | 9/2001 | Besson et al. |
| 6,302,844 B1 | 10/2001 | Walker et al. |
| 6,330,426 B2 | 12/2001 | Brown et al. |
| 6,330,457 B1 | 12/2001 | Yoon |
| 6,334,778 B1 | 1/2002 | Brown |
| 6,337,918 B1 | 1/2002 | Holehan |
| 6,337,919 B1 | 1/2002 | Dunton |
| 6,368,273 B1 | 4/2002 | Brown |
| 6,375,469 B1 | 4/2002 | Brown |
| 6,375,614 B1 | 4/2002 | Braun et al. |
| 6,379,301 B1 | 4/2002 | Worthington et al. |
| 6,381,577 B1 | 4/2002 | Brown |
| 6,402,691 B1 | 6/2002 | Peddicord et al. |
| 6,404,862 B1 | 6/2002 | Holt |
| 6,440,069 B1 | 8/2002 | Raymond et al. |
| 6,441,747 B1 | 8/2002 | Khair et al. |
| 6,454,705 B1 | 9/2002 | Cosentino et al. |
| 6,478,736 B1 | 11/2002 | Mault |
| 6,493,437 B1 | 12/2002 | Olshansky |
| 6,525,670 B1 * | 2/2003 | Doi et al. .............. 340/870.16 |
| 6,558,320 B1 | 5/2003 | Causey et al. |
| 6,577,893 B1 | 6/2003 | Besson et al. |
| 6,579,231 B1 | 6/2003 | Phipps |
| 6,589,169 B1 | 7/2003 | Surwit et al. |
| 6,594,523 B1 | 7/2003 | Levine |
| 6,595,929 B2 | 7/2003 | Stivoric et al. |
| 6,599,250 B2 | 7/2003 | Webb et al. |
| 6,602,191 B2 * | 8/2003 | Quy .............. 600/300 |
| 6,611,705 B2 | 8/2003 | Hopman et al. |
| 6,638,218 B2 | 10/2003 | Bulat |
| 6,643,542 B1 * | 11/2003 | Kawanishi ............ 600/547 |
| 6,658,287 B1 | 12/2003 | Litt et al. |
| 6,694,186 B2 | 2/2004 | Bardy |
| 6,725,209 B1 | 4/2004 | Iliff |
| 6,749,537 B1 * | 6/2004 | Hickman ............ 482/8 |
| 6,770,029 B2 | 8/2004 | Iliff |
| 6,840,904 B2 | 1/2005 | Goldberg |
| 2001/0012201 A1 | 8/2001 | Fries et al. |
| 2001/0048025 A1 | 12/2001 | Shinn |
| 2001/0048359 A1 | 12/2001 | Yamane et al. |
| 2001/0051924 A1 | 12/2001 | Uberti |
| 2002/0003892 A1 | 1/2002 | Iwanaga |
| 2002/0010857 A1 | 1/2002 | Karthik |
| 2002/0022973 A1 | 2/2002 | Sun et al. |
| 2002/0106077 A1 | 8/2002 | Moquin et al. |
| 2002/0120200 A1 | 8/2002 | Brockway et al. |
| 2002/0122415 A1 | 9/2002 | Chang et al. |
| 2002/0133377 A1 | 9/2002 | Brown |
| 2002/0152391 A1 | 10/2002 | Willins et al. |
| 2002/0174345 A1 | 11/2002 | Patel |
| 2003/0046557 A1 | 3/2003 | Miller et al. |
| 2003/0081752 A1 | 5/2003 | Trandal |
| 2003/0126593 A1 * | 7/2003 | Mault .............. 725/10 |
| 2004/0034286 A1 | 2/2004 | Kasper et al. |
| 2004/0059599 A1 | 3/2004 | McIvor |
| 2004/0102683 A1 * | 5/2004 | Khanuja et al. .............. 600/300 |
| 2004/0152957 A1 | 8/2004 | Stivoric et al. |
| 2004/0152993 A1 | 8/2004 | Bardy |
| 2004/0167580 A1 | 8/2004 | Mann et al. |

OTHER PUBLICATIONS

"Micropaq," Wlch Allyn, http://www.monitoring.welchallyn.com/products/wireless/micropaq.asp, retrieved Apr. 16, 2003, 2 pages.

Home Health Telemanagement Service, The University of Illinois at Chicago Medical Center, http://www.uic.edu/hsc/acad/intmed/cardio/monitor/, retrieved Jul. 13, 2005, 1 page.

Boston Medical, http://www.bosmedtech.com/, retrieved Oct. 10, 2001, 2 pages.

Kivalo: Wireless Healthcare Informatics, http://www.kivalo.com/, retrieved Oct. 10, 2001, 2 pages.

(56) References Cited

OTHER PUBLICATIONS

"Digital Angel: Making Your World a Little Safer . . . ," http://www.digitalangel.net/da/, retrieved Oct. 10, 2001, 7 pages.
Cadionet, http://www.cardionet.com/, retrieved Oct. 10, 2001, 1 page.
The HomMed Central Station, http://www.hommed.com/patients_families/central_station.asp, retrieved Oct. 10, 2001, 1 page.
"BodyMedia Introduces SenseWear Pro Armband Wireless Body Monitoring Device," http://www.thinkmobile.com/news/00/39/23/, retrieved Oct. 10, 2001, 3 pages.
U.S. Appl. No. 10/868,676, Goldberg.
U.S. Appl. No. 10/963,205, Goldberg.
U.S. Appl. No. 11/108,355, Goldberg.
U.S. Appl. No. 11/356,739, Goldberg.

\* cited by examiner

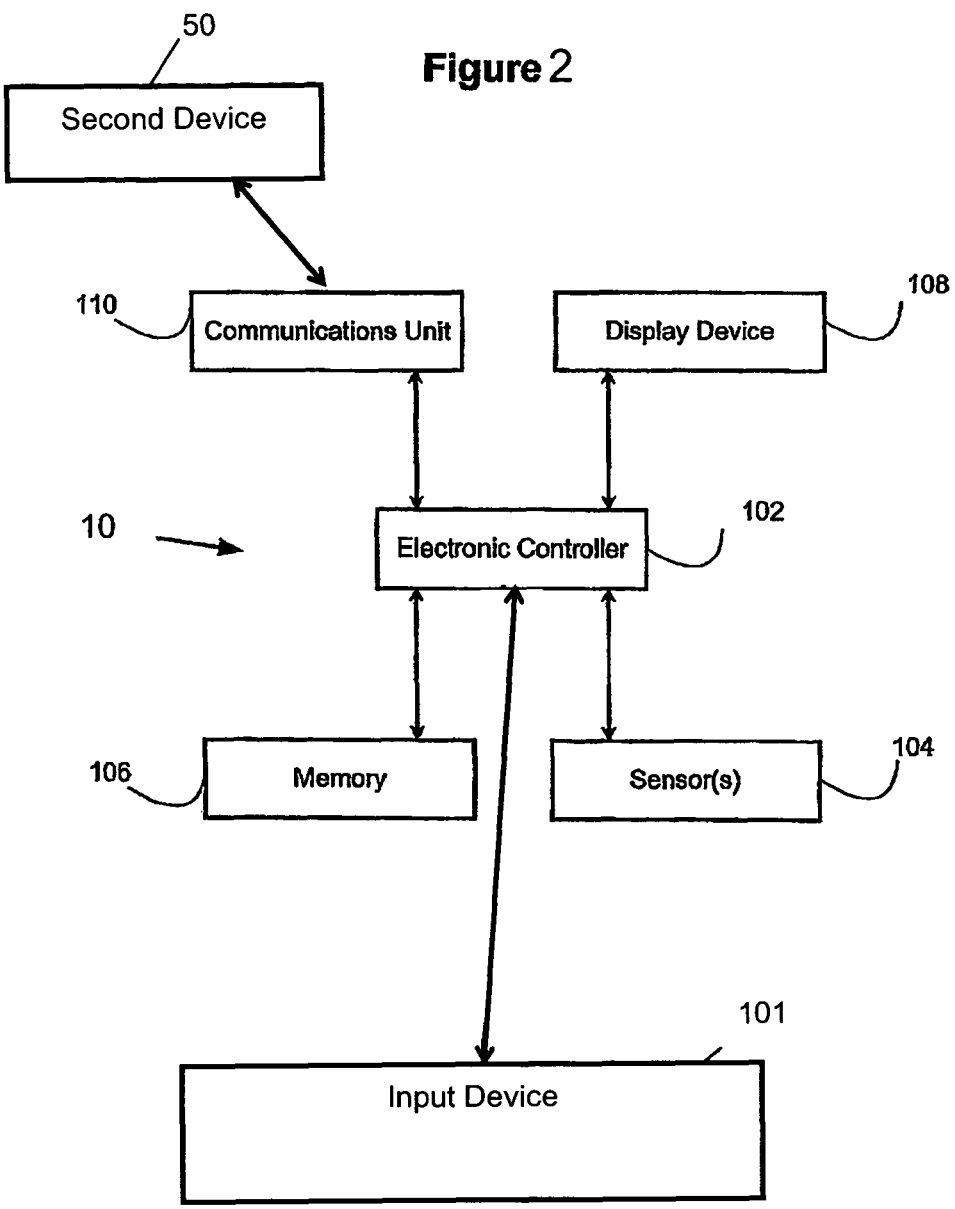

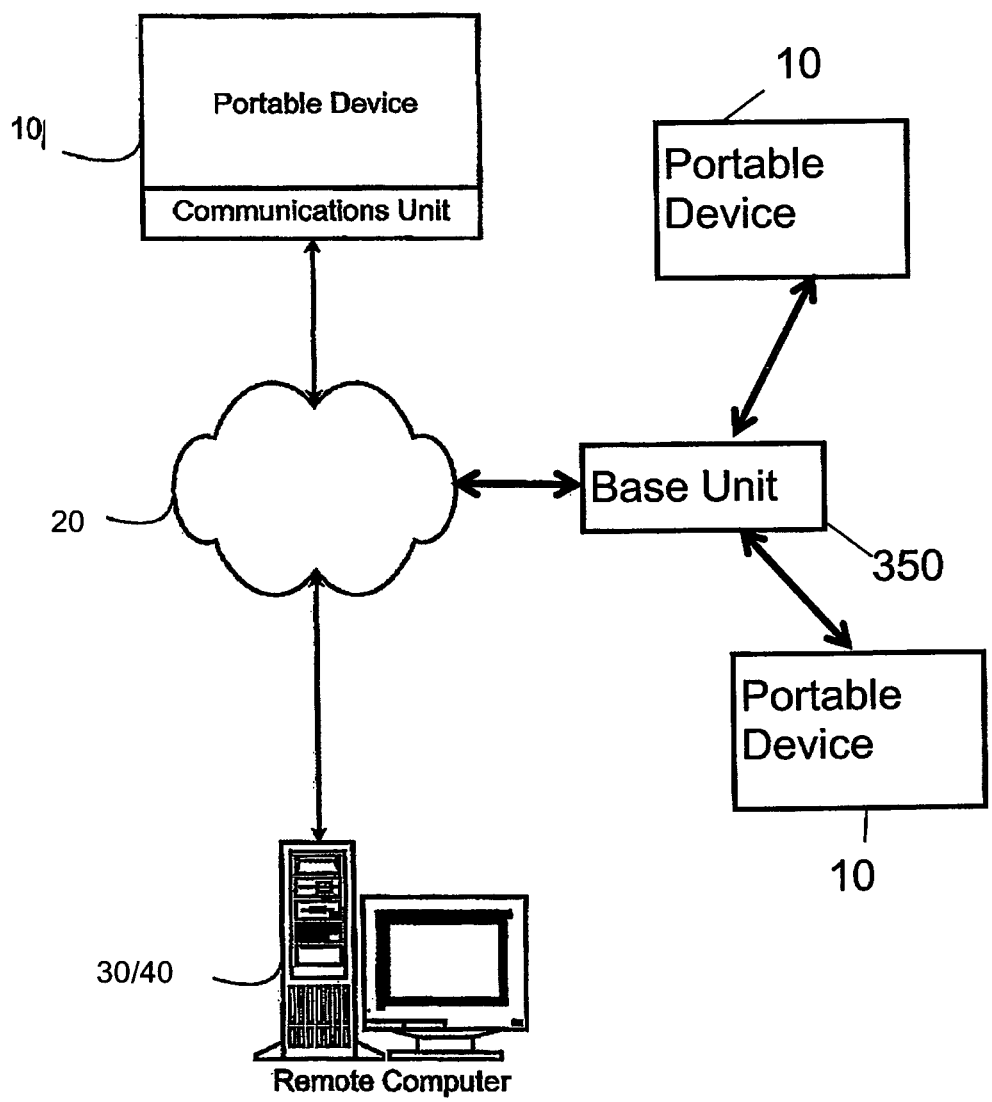
Figure 3

PERSONAL HEALTH MANAGEMENT DEVICE, METHOD AND SYSTEM

This application claims the priority of application Ser. No. 60/493,904, titled PERSONAL HEALTH MANAGEMENT DEVICE, METHOD AND SYSTEM, which was filed on Aug. 7, 2003, the disclosure of which is incorporated herein by reference in its entirety.

BACKGROUND OF THE INVENTION

The present invention relates generally to an interactive weight management device, method and system. This application incorporates by reference the entire disclosures of application Ser. No. 09/975,097, titled MEDICAL MONITORING DEVICE AND SYSTEM, filed Oct. 11, 2001, application Ser. No. 60/562,876, titled MEDICAL MONITORING SYSTEM, filed Apr. 16, 2004, application Ser. No. 60/487,471, titled MEDICAL MONITORING/CONSUMABLES TRACKING DEVICE, filed Jul.15, 2003, and application Ser. No: 10/892,520, titled MEDICAL MONITORING/CONSUMABLES TRACKING DEVICE, filed Jul. 15, 2004.

In developed countries, there is much interest in personal health and fitness, however as countries become industrialized there is a trend towards a sedentary lifestyle. Currently, there are an estimated 1.7 billion people in the world that are considered overweight or obese, including more than half of all Americans, Canadians, Australians and Britons. By overweight, it is meant that the subject has exceeded acceptable weight range and/or percent body fat generally considered as healthy determined by factors including, but not necessarily limited to age, height, sex, and body type. Being overweight or obese contributes in development of certain conditions, such as diabetes, heart disease, stroke, hypertension, osteoarthritis, sleep apnea and other breathing problems, some forms of cancer, high blood cholesterol, and psychological disorders such as depression. In one poll, more than half of American consumers said they have dieted or are currently dieting. Americans spend $33 billion annually on the numerous weight-loss products and services available to consumers, yet more than half of the United States population is overweight.

BRIEF SUMMARY OF THE INVENTION

The invention provides for offering, capturing, etc., from individuals, data related to one or more aspects of personal health, such as body weight, body fat percentage, etc., providing the data to a storage device remote from where the data was obtained and providing messages to or interacting with the respective individual relating to the aspect of personal health and the data. For example, in an application of the invention to weight management and/or fitness, and individual provides data for use in weight management, such as weight, body fat percentage, and/or body messages (e.g., messages related to body measurements, such as height, etc.) via a communication link to a weight management service or healthcare provider, such as doctors, nurses, personal trainers, nutritionists, dietician, or any other person or entity that provides or may otherwise assist a user with a weight management program, collectively "healthcare providers," who stores the data and provides messages to the individual, such as encouragement or requesting information on that individual's recent food intake and/or physical activity. The healthcare provider may process the data and use it for many purposes, including statistical purposes and tracking an individual's progress, etc. The invention provides devices, systems and methods for achieving the foregoing and other functionality described herein.

In one aspect of the present invention, a device is provided to monitor, offer, collect, etc. and communicate weight management data for managing the weight of at least one user, such as body weight or body fat percentage data. In one embodiment, the device is portable and provides interactive communication between users and healthcare providers over a network.

In one embodiment, the device includes a display, keypad, an electronic controller, a wireless module and/or communication unit, and an electronic memory device to store data. The device communicates with measurement devices to obtain measured weight management data. This may be done over an entirely wireless link, a wired link or a combination of both. The device also preferably communicates over a network, such as the Internet, to authorized parties, such as a healthcare provider (which may also function as a partner to provide the inventive method or aspect thereof or related thereto), which stores the information and provides access to the information for authorized parties. The wireless module and/or communication unit may include an internal modem, wireless transmitter/receiver combination, etc. A user may input data or other information into the keypad to store to the device and/or communicate to the healthcare provider. The device may also be connected to a mobile telephone or a computer, wirelessly, by wire, or both.

In one embodiment, the device includes a sensor, to measure weight management data, such as body fat percentage.

In one embodiment, the invention provides means for communicating user-focused messages to the device, in response to data communicated by a user, such as a weight measurement, from the healthcare provider to the user. For example, the messages may be words of encouragement or provide menus or exercise programs. The device also provides means for the user to communicate with the healthcare provider and/or interactively respond to the healthcare provider's messages. For example, the messages from the healthcare provider may prompt for information relating to food intake, physical exercise, etc.

In another aspect of the invention, a first personal health management device is provided that includes an electronic controller and at least one memory device which cooperate to store at least temporarily weight management data for managing the weight of at least one user obtained from at least one component for obtaining such data, and a communications unit for communicating the data obtained to a healthcare provider for monitoring progress with respect to a weight management program over a network. The communications unit may communicate the data to a base unit, e.g., wirelessly, which communicates the data over the network via a wireless and/or wired link or lings. Alternatively, the communications unit may communicate the data directly to the network.

Various types of weight management data may be used to monitor the user's progress, such as a user's weight, a user's body fat percentage, exercise data, food consumption data, or a combination thereof. Similarly, various components may be used to obtain weight management data, such as a keypad, a body fat percentage sensor for measuring a user's body fat percentage, a scale for measuring a user's weight, an exercise machine, a food scale, etc., which components may be integrated within the device or within a second device communicatively enabled to provide the data obtained to the personal health management device.

In one embodiment, the personal health management device includes a display device for displaying messages communicated to the device from the healthcare provider in response to the weight management data communicated to the healthcare provider. The device may further allow the user to interactively respond to messages communicated thereto from the healthcare provider.

In another aspect of the invention, a personal health management system is provided that includes at least one computer which can communicate with at least one personal health management device over a communication network. The personal health management device is generally capable of obtaining weight management data, such as a user's weight, a user's body fat percentage, exercise data, and a user's food consumption data, that is obtained from at least one component for obtaining such data, and communicating the data obtained to the at least one computer for monitoring progress with respect to a weight management program.

In one embodiment, the at least one computer communicates a message to the personal health management device in response to weight management data received therefrom. Various types of messages may be communicated, including messages that include words of encouragement. In one embodiment, the message includes information regarding at least one of a menu or exercise program that has been adjusted based on the weight management data received from the user.

In another aspect of the invention, a method for managing personal health is provided that includes receiving weight management data for managing the weight of at least one user, such as a user's weight, a user's body fat percentage, exercise data, and a user's food consumption data, over a network, and monitoring the user's progress with respect to a weight management program. The data is for at least one user is generally obtained with a personal health management device. In one embodiment, the method includes communicating a message to the personal health management device in response to data received therefrom, such as messages including information regarding at least one of a menu or exercise program adjusted based on the weight management data received.

BRIEF DESCRIPTION OF THE DRAWINGS

The invention is illustrated in the figures of the accompanying drawings which are meant to be exemplary and not limiting, in which like references are intended to refer to like or corresponding parts, and in which:

FIG. 2 is a block diagram of a personal health management device according to one embodiment of the invention.

FIG. 3 is a block diagram of a personal health management system according to another embodiment of the invention.

DETAILED DESCRIPTION

Figure 1:
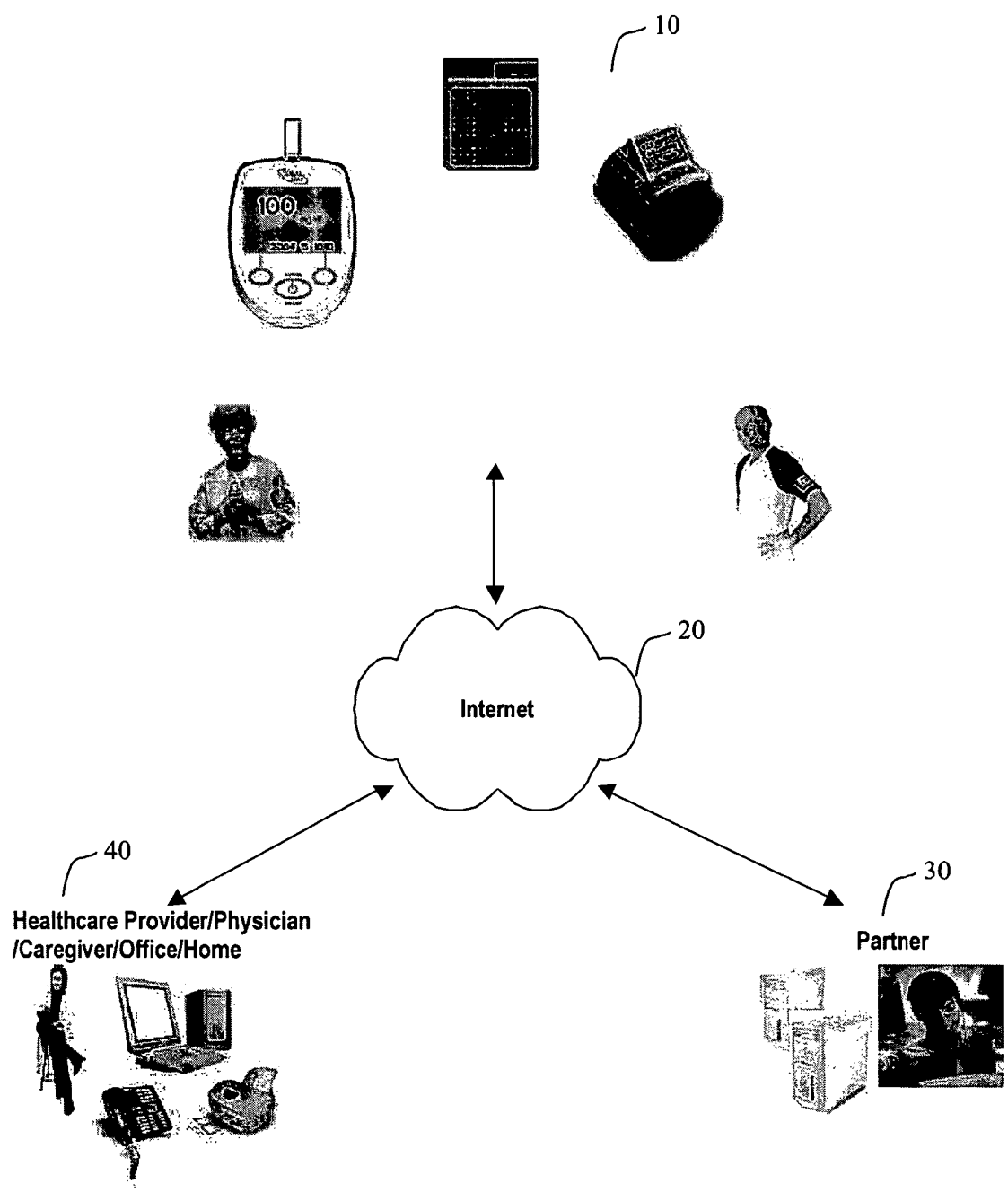
FIG. 1 is a diagram showing a view of a personal health management system according to one embodiment of the invention.

A preferred embodiment of a personal health management device, method and system provides for communication between a user and a healthcare provider with respect to weigh management and/or physical fitness. Preferred embodiments of the invention are now described with reference to the drawings.

Referring to FIG. 1, in one embodiment of the invention, a personal health management device 10 is provided that generally communicates data for use in managing the weight of at least one user in a weight management program, such as weight, body fat, or a combination thereof, captured or obtained therewith with a healthcare provider 40 or partner 30, over the Internet or other communications network 20.

The device 10 is preferably portable and includes means to monitor and communicate data related to weight management, such as body weight or body fat percentage. Referring to FIG. 2, in one embodiment, the device 10 preferably includes at least one of a display device 108, keypad or other type of input device 101, an electronic controller 102, a wireless module and/or communication unit 110, and an electronic memory to store data 106. The display 108 may be an LCD screen or other display known in the art. The input device 101, e.g., the keypad, provides a user the means to input data or information into the device, and may include any keypad or data input interface known in the art. Alternatively, the display and keypad may be provided together in a single interactive touch screen.

The wireless module and/or communication unit 110 generally provides wireless communication between the device 10 and the healthcare provider 40 or partner 30 over the network 20, thereby allowing a remote user to communicate with a healthcare provider 40 or partner 30 regarding a weight management program. The wireless module and/or communications unit 110 may utilize an internal modem, wireless transmitter/receiver combination or cellular technologies. The electronic memory 106 may be any storage facility, such as a microchip, to provide data storage. In other embodiments, the device 10 may communicate over a wired link to a telephone line, computer, PDA, cell phone, or any other communicatively enabled device.

Data may be obtained with the device 10 with appropriate components for obtaining weight management data, such as scale or other means for measuring user weights, a body fat percentage sensor/device, keypad, etc., integrated within the device 10. In one embodiment, the data is obtained from at least one other or second device 50 separate from the device 10 each separate device including at least one component for measuring or otherwise obtaining the relevant data. In this instance, the wireless module and/or communications unit 110 also provides communication between the device 10 and a second device 50, such as a scale, ruler, caliper, etc., which measures or otherwise determines weight management data for managing the weight of a user, e.g., weight, height or any other body dimension, etc. In another embodiment, the device 10 and/or the second device 50 includes one or more sensors 104 to measure weight management data, such as a sensor that uses an electric current to measure body fat percentage. For example, in this instance a user stands on a scale and the scale communicates wirelessly or via a wired link the measurements, e.g., weight, body fat percentage, height, etc. to the device 10. Preferably, the device 10 receives the measurements obtained by a second device 50 or sensor 104, e.g., the body fat measurement sensor, directly in a wireless transmission, thereby eliminating the potential for human error, intentional or unintentional, and the need for a connector, other intermediary device or communicating device to obtain the measurement to transmit to the healthcare provider 40 and/or partner 30.

The second device 50 may be any device used in weight management program. For instance, the device 50 may be an exercise device, such as a treadmill, bicycle, universal weight station, etc., enabled to obtain exercise data and communicatively enabled to communicate the exercise data to the communications unit 110 of the device 10. For example, a treadmill may track duration of use, speed, the user's heart rate, etc., and communicate the exercise data to the device 10. The exercise data may then be used to track the user's progress with an exercise program in connection with a weight management program and/or determine calories used, aerobic capacity, etc. The device 50 may similarly include a device for obtaining data regarding the user's food consumption, such as be a scale for weighing food and determining therefrom the user's caloric intake, compliance with a suggested menu, etc.

In another embodiment, the input device 101 serves as the component for obtaining data, in which instance the user manually inputs some or all of his or her measurements, e.g., weight, fat percentage, height or other measurements, age, etc., caloric data, exercise data, etc. into the device 10 via the input device 101, e.g., the keypad. In another embodiment, the device 10 is communicatively coupled to the second measuring device 50, for example, with wires with an appropriate plug or cradle interface for linking the devices 10, 50, and the measurement is sent to the device 10 over the wires.

Referring to FIG. 3, in one embodiment, the device 10 communicates through a base or local unit 350 which, e.g., services one or more associated devices 10, e.g., by relationship, such as a family, household, medical group, etc. relationship, or by location, etc. The base station 350 beneficially allows a plurality of devices 10 to interface with a single communicatively enabled device for communicating data to the remote computer, which is particularly useful in instances where a plurality of devices 10 are used in a single location, such as a hospital, a household, etc., with a limited amount of communicatively enabled devices.

The healthcare provider 40 may be a dietician, nutritionist, physician, caregiver, personal trainer, office, home, service or other person or entity providing weight management information or weight management services. The partner 30 may be a third party weight management information provider or data collector. For example, the partner 30 may provide e.g., suggested menus or exercise programs, monitor progress with respect to a weight management program, the suggested menus, or exercise programs, and collect information related to the user's results based on such menus or exercise programs and adjust the weight management program, menus or exercise program appropriately.

In a preferred embodiment, a measurement of weight management data is obtained by the device 10, for example, by wireless communication from a measuring device 50, such as a scale, or manually entered by a user, or via a sensor 104 on the first device 10 or second device 50, as described herein. Preferably, the measurement is obtained at regular time intervals, such as daily or weekly. The measurement as well as other data discussed herein may be stored locally to the device 10 storage and/or sent over the network 20 to the healthcare provider 40 and/or partner 30 automatically at a given time, or pursuant to manual direction. The data obtained may be used, for example, to chart the user's progress with regard to the weight management program, identify particular sticking points, and adjust the weight management program appropriately based on the data collected.

In one embodiment, the healthcare provider 40 and/or partner 30 responds to the sent measurement with a communication, such as a message, over the network 20, that is delivered to the device 10. The communication provides interactive two-way communication between a remote user and a healthcare provider 40 and/or partner 30 relating to weight management, exercise program, menu, etc.

The communication may be for example, a message of encouragement for a weight loss or weight gain, as compared to a previous measurement, depending on the user's weight management goals. In this case, the encouragement message may also be sent to devices belonging to members of a group associated with the user, for example, persons in a weight loss group or community, to provide encouragement to the user and the other group members.

Also, the communication may be in the form of a questionnaire related to for example, recent diet and exercise. The communication may also be in the form of menus or exercise programs and may be provided directly to the device 10, or provided in the form of a message indicating that the menu or exercise program may be obtained from a particular source, for example, a local branch office of the healthcare provider 40 or partner 30, or a particular website. The user may respond to the communication, e.g., prompts, by entering or selecting responses to the questionnaire into the device 10, and transmitting the responses over the network 20 to the healthcare provider 40 and/or partner 30, thus interactively communicating remotely with a healthcare provider 40 or partner 30 to enhance a weight management program. The menus or exercise programs may be adjusted based on the user's progress with respect to the weight management program monitored with data received with the device. For example, if the user's progress, e.g., weight or body fat percentage has not changed for a consecutive period of time, the menu may be adjusted to lower caloric, fat, carbohydrate, intake, etc., and/or the exercise program may be adjusted to increase cardiovascular or any other type of exercise.

What is claimed is:

1. A monitoring system for use in managing weight of at least one subject, the monitoring system being adapted to communicate with a remote computer over a communications network, the monitoring system comprising a monitoring device and a local base unit, the monitoring device comprising:
a scale which obtains weight data of a subject;
an input device;
a display device, the monitoring device being configured to display on the display device weight data obtained by the scale; and
at least one communications unit which wirelessly transmits weight data and messages based on input from the input device to the local base unit and which receives at least messages from the local base unit;
the monitoring device being configured to display on the display device messages based on input from the input device and messages received by the at least one communications unit from the local base unit;
the local base unit being configured to (a) receive the weight data and the messages wirelessly from the monitoring device without passing through the communications network, (b) transmit the weight data and the messages received from the monitoring device over the communications network for receipt by the remote computer without the local base unit displaying the weight data and messages received from the monitoring device, (c) receive at least messages over the communications network provided by the remote computer and (d) wirelessly provide at least the messages received over the communications network to the monitoring device without the local base unit displaying the messages received from the remote computer;
wherein the monitoring device and the local base unit are located on a same side of the communications network such that communications therebetween do not pass thorough the communications network and the local base unit communicates over the communications network with the remote computer, and the local base unit is configured to communicate with the monitoring device and with the remote computer without operation of a user interface.

2. The system of claim 1 wherein the monitoring device comprises a weight management device incorporating the display device and the input device, and wherein the scale is separate from the weight management device and is configured to wirelessly transmit weight data.

3. The system of claim 2 wherein the weight management device includes a wireless communications unit which receives weight data from the scale, an electronic controller and a memory device, the electronic controller causing weight data received by the communications unit to be stored in the memory device at least temporarily, the electronic controller providing weight data and messages for display on the display device.

4. The system of claim 1 wherein the monitoring device is configured to receive data from at least one sensor in addition to receiving weight data from the scale.

5. The system of claim 1 comprising another monitoring device configured to communicate with the local base unit, the other monitoring device being configured to receive data from at least one sensor.

* * * * *